(12) United States Patent
Skripitsyna

(10) Patent No.: US 9,532,589 B2
(45) Date of Patent: Jan. 3, 2017

(54) CONSORTIA AND STRAINS OF MICROORGANISMS, AND METHODS OF USE THEREOF

(76) Inventor: Mariya Andreevna Skripitsyna, Moscow (RU)

( * ) Notice: Subject to any disclaimer, the term of this patent is extended or adjusted under 35 U.S.C. 154(b) by 85 days.

(21) Appl. No.: 14/112,760

(22) PCT Filed: Apr. 18, 2012

(86) PCT No.: PCT/RU2012/000296
§ 371 (c)(1),
(2), (4) Date: Jan. 6, 2014

(87) PCT Pub. No.: WO2012/144937
PCT Pub. Date: Oct. 26, 2012

(65) Prior Publication Data
US 2014/0141123 A1  May 22, 2014

(30) Foreign Application Priority Data
Apr. 19, 2011 (RU) .................. 2011115345

(51) Int. Cl.
| | |
|---|---|
| *A23L 2/38* | (2006.01) |
| *A23F 3/16* | (2006.01) |
| *A23L 2/385* | (2006.01) |
| *C12N 1/20* | (2006.01) |
| *C12R 1/01* | (2006.01) |
| *C12R 1/645* | (2006.01) |
| *C12G 3/02* | (2006.01) |

(52) U.S. Cl.
CPC ............... *A23L 2/382* (2013.01); *A23F 3/166* (2013.01); *A23L 2/385* (2013.01); *C12G 3/025* (2013.01); *C12N 1/20* (2013.01); *C12R 1/01* (2013.01); *C12R 1/645* (2013.01)

(58) Field of Classification Search
CPC ............ A23L 2/382; C12R 1/01; C12R 1/645; C12G 3/025
USPC ......................................... 426/60; 435/256.8
See application file for complete search history.

(56) References Cited

U.S. PATENT DOCUMENTS 4,948,728 A * 8/1990 Stephanopoulos .... C12M 23/20
                                                    435/174

OTHER PUBLICATIONS

Jayabalan, R. et al. Food Sci. Biotechnol. 19: 843-847 (2010).*
Groleau, D. et al. Biotechnology Letters. 17: 315-320 (1995).*
Choi, K-H et al. J. Korean Soc. Food Sci. Nutr. 33: 176-181 (2004).*
Malbasa, et al. "Sucrose and Inulin Balance During During Tea Fungus Fermentation." Roum. Biotechnol. Lett., vol. 7 (1): 573-76 (2001).
Malbasa et al. "Ribonucleic Acids in Different Tea Fungus Beverages." APTEFF, vol. 34 (1): 103-10 (2003).

* cited by examiner

*Primary Examiner* — Hamid R Badr
(74) *Attorney, Agent, or Firm* — Porzio, Bromberg & Newman, P.C.

(57) ABSTRACT

Invention relates to biotechnology, food industry and concerns to microbial consortia and microbial and yeast strains, as well as to methods for producing by integrated technological cycle with the use of consortia and microbial and yeast strains from the fermented base, which is a semi-product of bread kvass, fermented kvass, nonalcoholic kvass, as well as to methods for producing tea fungus culture fluid, tea-fungus concentrates, kombucha beverages, and vegetable extracts in a single technology process.

5 Claims, No Drawings

CONSORTIA AND STRAINS OF MICROORGANISMS, AND METHODS OF USE THEREOF

FIELD OF THE INVENTION

This invention relates to biotechnology, food industry and concerns to microbial consortia and strains of bacteria and yeasts, and is directed to methods for producing a fermented base in the form of a semi-finished product of bread kvass fermentation kvass and alcohol-free kvass in a single process cycle with the aid of consortia and strains of bacteria and yeasts as well as to methods for producing a liquid kombucha culture, kombucha concentrates and kombucha drinks and vegetable extracts in a single process cycle.

BACKGROUND OF THE INVENTION

Generally, currently used methods of preparing beverages consist in preparation of sugar syrup and blending of various types of raw materials (juices, extracts, water, flavoring agents etc.). In manufacturing kvass, beer, and honey beverages, the fermentation of prepared beverage bases is used followed by filtration, and if necessary hereafter by ripening of the obtained beverage or beverage base [Digests of recipes for non-alcoholic beverages, kvass from the bread raw materials. Moscow, 1983].

A method for making a non-alcoholic beverage by mixing sugar, kombucha concentrate, water-soluble melanin, water-alcohol solution of melissa with water in the presence of carbon dioxide and beverage ripening at temperature 7-10° C. is known (Patent RU 2210952). "Tea fungus" (Kombucha; Japanese fungus) represents a symbiosis of yeast and acetic-acid bacterium, which forms a film at the surface of the sweet tea infusion. The yeast fermenting sugar promote to the formation of a small amount of alcohol and carbon dioxide, and the acetic-acid bacteria ferment sugar with the release of acetic acid, consequently the obtained fluid (tea kvass) acquires a sweet-and-sour taste and is slightly carbonated [Great Soviet Encyclopedia ( Б.С. Э.), 1978, Moscow, Sovetskaia Entsiklopediya].

Patent RU No. 2153816 describes a beverage and a method for manufacturing for this beverage and for the culture medium to manufacture the beverage based on growing the tea-fungus biomass (zooglea) in a tea infusion with a sugar-containing product. A culture fluid obtained as a result of incubation of tea fungus zooglea under aerobic conditions in a nutritional sugar-containing medium followed by incubation under anaerobic conditions at a temperature from 12 to 40° C. during from 2 to 150 days, is used for preparing a beverage base. The base consists of the culture fluid and of a tea extract with a sugar-containing product. The base is ripened under anaerobic conditions, that is accompanied with a decrease of a dry solids weight ratio. According to a method of the invention biological activity of beverages depends on the incubation time. One of the shortages of the known method is a long duration of obtaining a beverage having the highest biological activity.

There is a known method for making a fruit-bread kvass, said method comprising using a yeast culture and obtaining a beverage enriched with useful substances compared to a common kvass due to adding fruit juices (RU 2337592), as well as a method for making an alcohol-free beverage, which comprises using a tea fungus culture and obtaining a pear-tasted beverage due to using fruit wastes as substrates (SU 1477364).

Patent RU 2337592 describes a method for beverage preparing based on the use of tea fungus in fermentation of tea and other sugar-containing products by gradual fermenting comprising pre-fermenting these sugar-containing products with the use of a yeast culture, other than a tea fungus culture, and then fermenting with the use of a tea fungus culture. A method for making a beverage having a biological activity includes the fermentation of a sugar-containing fluid in the presence of a tea fungus culture, the said method including initial fermenting a sugar-containing fluid with the use of another yeast culture during a period from 1 hour to 14 days at a temperature from 20 to 40 degrees, and the fermentation in the presence of a tea fungus culture is carried out during a time period from 10 hours to 30 days. The beverage should be desirably clarified at a temperature of not more than 15° C. A sugar-containing fluid obtained by mixing water and sugar or jam or honey is used. Also, a sugar-containing fluid with addition of a fruit juice is used. Initial fermentation of a sugar-containing fluid with the use of a yeast culture (baker's yeast, or wine yeast, or other yeast cultures), followed by the repeat fermentation in the presence of a tea fungus culture produces a beverage, which is free of yeast aftertaste and of 'dryness' native to the traditional kvass.

Patent RU228012 describes a beverage preparing method including the fermentation of a sugar-containing water solution with addition of a tea fungus under aerobic conditions and its filtration, before obtaining the sugar-containing water solution the preliminary filtered and disinfected water being processed with natural minerals (such as chalcedony, Cambay stone, or quartz) by adding minerals to water and maintaining them in the solution during the whole fermentation process. The fermentation is carried out in three stages during 28-24 days at stepdown decrease of temperature from 32-30° C. to 28-25°. The persistence of minerals in water promotes to a positive growth of tea fungus microbial culture and prevents the growth of foreign microorganisms that do not belong to the natural symbiotic composition of tea fungus.

Patent RU2280394 describes compositions based on a combination of fermentation products of tea fungus (symbiosis of yeast and acetic acid bacteria) and chaga mushroom, which are obtained by the fermentation of a blend of a sugar-containing substance, tea fungus culture fluid and chaga mushroom extract (RU2280394). The fermented blend is additionally ripened under anaerobic conditions and/or at a temperature of not more than 10° C. Compositions are also obtained, which include a sugar-containing component, tea fungus zooglea and chaga mushroom extract by mixing a preliminary fermented composition consisting of sugar, tea fungus culture and chaga mushroom extract by fermenting the obtained mixture, kvass being used as a preliminary fermented composition.

A method for preparing a tea fungus zooglea has been described, which includes mixing a tea fungus culture with sugar and fluid, other than tea, followed by and fermenting the obtained mixture, a fruit or berry juice being potentially used as a fluid. So tea fungus zooglea was obtained by adding a tea fungus culture into a solution of blackcurrant juice. A solid fraction of the obtained zooglea was used as an additive for imitation of dry fruits in bakery manufacturing (a microbial depressing effect was achieved simultaneously for bakery products). The end fermentation of kvass wort, fermented with the use of common yeast cultures (bakery yeast), based on the tea fungus culture, allowed to obtain a beverage, similar to kvass but having a less degree of foaminess and more acid flavor.

However, microorganisms forming a tea fungus consortium, which are used for obtaining beverages in described methods, have not been identified, and moreover, compositions of consortia in various geographic areas are different, consequently, products have also different compositions and its standardization is very problematic.

Patent RU 2165711 describes the use of tea fungus microflora *Medusomyces gisevii* in a method for preparing a starter culture for fermented milk products. Skim milk is pasteurized, cooled to the temperature of fermentation, then tea fungus microflora *Medusomyces gisevii* is added directly into milk in the ratio tea fungus:milk 1:30, fermented at 20-24° C. during 20-28 hours to the formation of a clot with acidity of 95-100° T. The obtained starter culture is used for manufacturing fermented milk products.

Patent RU2081911 describes a consortium of yeast and bacteria and a method for making a low-alcoholic beverage on its base. The consortium of yeast and bacteria includes *Saccharomyces mandshuricus, Hausemaspora* sp, *Torulopsis globosa, Torulopsis* sp, *Saccharomyces Ludwigii, Saccharomyces lactis, Acetobacter xylinum, Acetobacter aceti,* and *Gluconobacter subaxydans* and produces a complex of vitamins, organic acids, enzymes and cellulose. The method provides for making a low-alcoholic beverage with the use of a consortium of yeast and bacteria by means of fermentation of raw material blend, consisting of a carbohydrate-containing substrate and a nitrogen source at a temperature 24-32° C. during 4-5 days. A liquid fraction is separated by filtration or centrifugation. The liquid fraction is used as a low-alcoholic tonic drink.

Disadvantage of the known method is that the used consortium is a inseparable community of yeast and bacteria, that does not allow to use valuable properties of separate microorganisms for creating a greater variety of products and improving its taste and health-giving potential as well as optimizing its manufacturing methods and developing integrated technologies of preparing tea fungus cultures, kombucha concentrates, and various beverages based on tea fungus cultures and concentrates.

Moreover, the efficacy of the known methods of preparing beverages with the use of tea fungus remains fairly low due to simultaneous formation of zooglea. Thus, the development of industrial production methods that allow significant speeding up improving the production process of beverages having various tastes and health-giving properties, is a crucial task, a solution of which potentially provides a possibility to produce standardized beverages having fine and various tastes.

SUMMARY OF THE INVENTION

The authors of the present invention introduce a novel method for making a fermented base representing a semi-product of bread kvass and intended for the industrial production of fermentation kvasses at plants lacking own fermentation lines, which is based on successive fermentation of carbohydrate-containing raw materials with the use of microbial cultures, the main fermentation being carried out with the use of bakery yeast, preferably, of yeast *Zygosaccharomyces bisporus*, followed by end fermentation with bacterial culture *Gluconoacetobacter hansenii* G-001 or consortium a *Medusomyces gisevii* alfa SA-10, that allows to lower the content of ethanol in the fermented base and to qualify this base as alcohol-free beverage.

According to the method of the invention, maltose concentrates, including kvass wort concentrate, barley-malt extract, high-maltose syrup, brewing syrup are used as carbohydrate-containing substrates. In one of the embodiments of the invented method, the fermented base for production of bread kvass is obtained with the use of a rye-malt extract as a carbohydrate-containing substrate and by performing the main fermentation stage with the use of yeast *Zygosaccharomyces bisporus* without an end fermentation stage.

In one of the aspects the invention relates to a method for making the fermented kvass on filling lines for non-alcoholic beverages at plants lacking own fermentation lines, which provides for mixing a fermented base obtained according to the method of the invention and other components according to the formula and diluting it with cold water saturated with carbon dioxide.

In another aspect, the invention discloses a method of making alcohol-free kvass, which provides for successive fermentation of carbohydrate-containing raw materials, wherein preliminary fermentation is carried out with the use of a culture of *Dekkera anomala* strain D-001, and the following fermentation is performed in the presence of *Gluconoacetobacter hansenii* G-001. Composition of non-alcoholic fermented kvass depends on raw material components (kvass wort concentrate, barley-malt extract, high-maltose syrup, brewing syrup, as well as syrups based on fruits, berries and vegetables).

In a further aspect, the present invention relates to the method for making a tea fungus culture fluid which provides for accelerated growth of a tea fungus consortium. In addition to accelerating preparation of tea fungus culture fluid by 15-20 times as compared to methods known from prior art, implementation of the method according to the present invention prevents to growth of zooglea that impedes mechanization and automation of production processes when using the known methods. Method for making tea fungus culture fluid according to the present invention provides for excess pressure aerating of carbohydrate-containing raw materials before starting zooglea formation, the growth medium being additionally mixed with the use of circulation. Fermentation of carbohydrate-containing raw materials is performed with the use of the consortium culture of Fungi Tea Sa-14, *Medusomyces gisevii* alfa Sa-10 or *Medusomyces gisevii* SA-12.

In one of the preferable embodiments of the invented method the preliminary fermentation is performed with the use of a culture of *Zygosaccharomyces bisporus* followed by end fermentation with a culture of Fungi Tea Sa-14, *Medusomyces gisevii* alfa Sa-10 or *Medusomyces gisevii* SA-12.

According to another aspect, the invention provides a method for making kombucha concentrates, which provides for the use of tea fungus culture fluid according to the present invention as a starter culture for a concentrated growth medium consisting of fermentable carbohydrates and plant raw materials. In one of the embodiments of the method for making kombucha concentrates the acidity is stabilized with the use of *Gluconoacetobacter hansenii* G-001 or lactic acid bacteria which are generally used as starter cultures.

Another aspect of the present invention relates to a method for making kombucha beverages, which provides for the fermentation of growth medium containing carbohydrate-containing syrup based on components according to the beverage formula, in the presence of a tea fungus culture, wherein the fermentation is carried out with the use of culture fluid according to the invented method for preparing culture fluid, until its acidity reaches formulation values for freshly prepared beverages.

And another aspect of the present invention relates to a method for making kombucha beverages, wherein filter-sterilized or sterilized tea fungus concentrate obtained according to the invented method for making kombucha concentrates, and components according to the beverage formulation are blended followed by pasteurization or not.

According to another aspect the invention provides consortia of Fungi tea Sa-14, *Medusomyces gisevii* Sa-12 and *Medusomyces gisevii* alpha Sa-10, producing a complex of vitamins, organic acids and enzymes.

In another aspect the invention provides strains of *Zygosaccharomyces bisporus*, *Gluconoacetobacter hansenii* G-001 and *Dekkera anomala* D001, which produce a complex of vitamins, organic acids and enzymes.

DETAILED DESCRIPTION OF THE INVENTION

The present invention provides a tea fungus culture Fungi Tea, producing a complex of organic acids, enzymes and deposited in the Russian National Collection of Industrial Microorganisms (VKPM), International Depository Authority, under accession number VKPM Sa-14.

The present invention provides a tea fungus culture *Medusomyces gisevii* alfa, producing a complex of organic acids, enzymes and vitamins, and deposited in the Russian National Collection of Industrial Microorganisms (VKPM), International Depository Authority, under accession number VKPM Sa-10.

The present invention provides a tea fungus culture *Medusomyces gisevii*, producing a complex of organic acids, enzymes and vitamins, and deposited in the Russian National Collection of Industrial Microorganisms (VKPM), International Depository Authority, under accession number VKPM SA-12.

The present invention is based on an unexpected discovery that the use of microbial strains isolated from symbiotic association of tea fungus, in particular, *Gluconoacetobacter hansenii* G-001, in the end fermentation of maltose concentrates, fermented with the use of any bakery yeast, preferably of yeast *Zygosaccharomyces bisporus*, allows to diminish the content of ethanol in the fermented base and to qualify this base as alcohol-free beverage and to obtain a semi-product of bread fermented kvass, intended for industrial production of fermentation kvasses at plants lacking own fermentation lines. Moreover, the use of microbial strains, separated from tea fungus symbiotic association, in particular, the use of *Dekkera anomala* D-001 during the fermentation of maltose concentrates and *Gluconoacetobacter hansenii* G-001 in the following end fermentation allows to obtain a non-alcoholic kvass, the taste of which is as good as a 'genuine' fermentation kvass.

In one of the aspects, the invention relates to a method for making tea fungus culture fluid, which provides accelerated growth of tea fungus microorganisms, capable actively to assimilate and ferment the nutritional mediums obtaining from carbohydrate-containing raw materials of various compositions. Moreover, in addition to accelerating preparation of tea fungus culture fluid by 15-20 times as compared to methods known from prior art, implementation of the method according to the present invention prevents to growth of zooglea that impedes mechanization and automation of production processes when using the known methods.

Consequently, in one of the aspects the present invention provides a method for making of fermented base for fermentation kvasses on filling lines for non-alcoholic beverages at plants lacking own fermentation lines, which provides for the successive fermentation of carbohydrate-containing raw materials, wherein the main fermentation is performed with the use of a culture of yeast, selected from the group comprising bakery yeast and *Zygosaccharomyces bisporus*, followed by the end fermentation by *Gluconoacetobacter hansenii* G-001 or *Medusomyces gisevii* alfa Sa-10 (Example 1)

According to the present invention are used as a carbohydrate-containing substrate maltose concentrates, including kvass wort concentrate, barley-malt extract, high-maltose syrup, brewing syrup.

In one of the embodiments of the invented method, the fermented base for production of bread kvass is obtained with the use of rye-malt extract as a carbohydrate-containing substrate, performing the main fermentation with the use of yeast *Zygosaccharomyces bisporus* without further end fermentation.

In one of the embodiments of the invented method for making of fermented base the main fermentation is performed with batch addition of fresh yeast culture portions and new portions of carbohydrate-containing raw materials (Example 1). Preferably, at the first stage fermentation with the use of a yeast culture is performed during at least 8 hours, after that fresh culture of yeast is added and fermentation goes on during next 18-36 hours, then to reach the initial density a maltose concentrate and culture fluid of Gluconabacter hansenii G-001 in amount of at least 5% of fermented blend volume are added into the blend; after the fermentation at a temperature of 35-38° C. during 18-36 hours a maltose concentrate and formulation constituents are added into the blend up to the full formulation norms followed by fermentation up to acidity value of 25 AD (acidity degrees). In the most preferable embodiment, at the first stage the fermentation with the use of a yeast culture is performed during 48 hours; after adding a fresh culture of yeast the fermentation continues during next 48 hours, then maltose concentrate is added up to the density of 17% and culture fluid Gluconabacter hansenii G-001 is added into the blend in amount of 10% of fermented blend volume; after the fermentation at a temperature of 35-38° C. during 24 hours maltose concentrate and formulation constituents are added into the blend up to the full formulation norms followed by fermentation up to acidity value of 25 AD.

In one more aspect the present invention provides a method for making fermented kvass on filling lines for non-alcoholic beverages at plants lacking own fermentation lines, which provides for mixing a fermented base obtained by the method according to the present invention and other components according to the formula and diluting the mixture with cold water saturated with carbon dioxide (Example 2). In one of the embodiments, method for making a fermented kvass provides for adding a dose of blend syrup (fermented base) into a bottle followed by diluting it with cold water saturated with carbon dioxide; in another embodiment, mixing water and blend syrup (fermented base) followed by saturating the blend with carbon dioxide is performed before bottle filling. For the first time, according to the invented method, bottling 'genuine' bread fermented kvass based on a semi-product a of bread kvass (fermented base) can be carried out on filling lines for alcohol-free beverages at plants lacking own fermentation lines.

In one more aspect, the invention provides a method of preparing nonalcoholic kvass, which provides for the successive fermentation of carbohydrate-containing raw materials, wherein preliminary fermentation is carried out with the use of a culture of *Dekkera anomala* strain D-001, and the following fermentation is performed in the presence of *Gluconoacetobacter hansenii* G-001. According to the method of the invention, maltose concentrates, including kvass wort concentrate, barley-malt extract, high-maltose syrup, brewing syrup, as well as syrups based on fruits, berries and vegetables are used as a carbon-containing raw material (Example 3).

Preferably, fermentation with the use of a culture of *Dekkera anomala* strain D-001 is performed at the first stage during 18-36 hours at a temperature of 30-32° C., afterwards fresh culture of *Dekkera anomala* D-001 is added and fermentation goes on during next 18-36 hours at a temperature of 30-32° C.; then maltose concentrate is added to reach the initial density and culture fluid of Gluconabacter hansenii G-001 is added into the blend in amount at least from 8% to 10% of fermented blend volume; after the fermentation at a temperature of 32-38° C. during 18-36 hours the maltose concentrate is added into the blend up to the full formulation norms followed by fermentation at a temperature of 36-38° C. ethanol to lower the ethanol content to values not more than 0.2% and to reach acidity at level not less 25 AD.

In the most preferable embodiment, at the first stage the fermentation with the use of a culture of *Dekkera anomala* strain D-001 is performed during 18-36 hours at a temperature of 30-32° C., afterwards a fresh culture *Dekkera anomala* D-001 is added in amount from 10% to 20.0% of fermented blend volume and fermentation goes on during next 48 hours at a temperature of 30-32° C.; the following fermentation is performed in the presence of Gluconabacter hansenii G-001 in amount from 10% to 20% of fermented blend volume at a temperature of 32-38° C. during 48 hours followed by fermentation at a temperature of 36-38° C. to lower the ethanol content to values not more than 0.2% and to reach acidity at level not less 25 AD.

In one of the aspects, invention relates to a method for making a tea fungus culture fluid, which provides for accelerated growth of tea fungus microorganisms capable actively to assimilate and ferment the nutritional mediums obtaining from carbohydrate-containing raw materials of various compositions. Moreover, along with accelerating a production of tea fungus culture fluid by 15-20 times as compared to methods known from prior art, the method according to the present invention prevents to growth of zooglea that impedes mechanization and automation of production processes when using the known methods. The method for making a tea fungus culture fluid according to the present invention provides for fermentation of carbohydrate-containing raw materials with the use of a tea fungus culture, before starting zooglea formation the carbohydrate-containing raw materials being aerated under pressure 0.4-0.7 atm and a growth medium being additionally mixed with the use of circulation (Example 4). Preferably, tea fungus culture is a culture from the consortium of Fungi Tea Sa-14, *Medusomyces gisevi* alfa Sa-10 or *Medusomyces gisevii* SA-12.

In one of the preferred embodiments, the preliminary fermentation is carried out with the use of a culture *Zygosaccharomyces bisporus* followed by end fermentation with Fungi Tea Sa-14, *Medusomyces gisevii* alfa Sa-10 or *Medusomyces gisevii* SA-12. Preferably, in the invented method of producing a tea fungus culture fluid according to the present invention a malt extract is used as carbohydrate-containing raw materials.

A tea fungus culture fluid obtained by the invented method is used to obtain kombucha concentrates according to the present invention and as a starter culture for a growth medium consisting of fermentable carbohydrates and plant raw materials, included into the formula for a certain beverage, in particular, in production of end kombucha beverages, cultured milk products, oat jelly beverages, nonalcoholic kvass, anti-hungover beverages, food supplements with antioxidant properties (Example 6).

Consequently, in one more aspect invention provides a method for making kombucha concentrates, which provides for the fermentation of a concentrated growth medium consisting of fermentable carbohydrates and plant raw materials, with a culture medium obtained by method of the invention (Example 5). In one of the embodiments the acidity is stabilized with the use of *Gluconoacetobacter hansenii* G-001 or lactic acid bacteria which are generally used as starter cultures.

Preferably, in the method for production of kombucha concentrates according to the present invention raw grain extracts preliminary hydrolyzed with the use of malts as a nutritional medium. The obtained concentrates are separated, filtered and sterilized to use in production of tea kvasses and non-alcoholic beverages on its base.

In a further aspect, the present invention provides a method for making kombucha beverages, wherein a filter-sterilized or sterilized tea fungus concentrate obtained according to the method of the invention, and components according to the end beverage formulation are blended, followed by pasteurization or not, to give stable kombucha beverages.

In a further aspect, the present invention provides a method for making kombucha beverages, which provides for the fermentation of growth medium containing carbohydrate-containing syrup based on components according to the beverage formula, in the presence of a tea fungus culture, wherein the fermentation is carried out with the use of culture fluid according to the method of the invention, until its acidity reaches formulation values for a freshly prepared beverage (Example 6). In accordance with the method for making kombucha beverages, tea and maltose concentrates, honey, skimmed milk, glucose and glucose-fructose syrups, fruits, berries and vegetables are used as a nutritional medium. In one of the embodiments of the method, vegetable juices deviled and salted are used as a nutritional medium and a culture from the consortium *Medusomyces gisevii* alfa Sa-10 is used as a culture fluid.

In another embodiment of the invented method for making of live kombucha beverages, a culture fluid obtained according to invention is added into a nutritional medium consisting of carbohydrate-containing raw materials based on components according to the beverage formula; and then, after the acidity reaches the formulation values for freshly prepared beverages, a starter culture of *Gluconoacetobacter hansenii* G-001 is added into the blend. The live tea fungus beverage is ready from the first day of bottling. The maturation of the beverage goes on in bottles during the whole shelf life. The beverage will not spoil with keeping during 3 and more years.

In another embodiment of the invented method for making kombucha beverages according to the present invention, after glass bottle filling the beverage is ripened in camera at a temperature from +30 to +35° C. until its acidity reaches formulation values for freshly prepared beverages, and afterwards it is subjected to tunnel pasteurization or autoclaving to obtain a pasteurized beverage which will not spoil with keeping during 180 days at a temperature from +2 to +25° C. Pasteurized beverages are also obtained based on tea and maltose concentrates, honey, glucose and glucose-fructose syrups, fruits, berries and vegetables.

In a further aspect, the present invention relates to a method for making vegetable extracts (fermented vegetable juices) fermented with a culture fluid of tea fungus, which is obtained according to the invention. The fermentation is performed at a temperature 8-12° C. up to acidity value of 10-12 AD.

According to one of the aspects, the invention provides a consortium of yeast and bacteria Fungi tea Sa-14, comprising *Zygosaccharomyces bisporus* and *Acetobacter aceti* 2, a consortium of yeast and bacteria *Medusomyces gisevii* Sa-12, comprising *Gluconacetobacter hansenii, Dekkera anomala* and *Picha membranaaefaciens*, and a consortium of yeast and bacteria *Medusomyces gisevii* alfa Sa-10, comprising *Gluconacetobacter xylinus, Brettanomyces anomalus* and *Zygosaccharomyces rouxii*, which produce a complex of vitamins, organic acids and enzymes and ferment carbohydrate-containing solutions. To obtain consortia according to the present invention the natural isolates of tea fungus has been subjected to the selection for microorganisms with health-giving properties on media containing glucose (about 10%) and tea at 25-30° C.

According to another aspect, the invention provides a *Zygosaccharomyces bisporus* strain isolated from a consortium of Fungi tea Sa-14, *Gluconoacetobacter hansenii* strain G-001 and *Dekkera anomala* strain D001, both isolated from a consortium of *Medusomyces gisevii* Sa-12, which produces a complex of vitamins, organic acids and enzymes.
Cultural-Morphological Characteristics:

On agarized complete yeasty medium, *Zygosaccharomyces bisporus* strain Y-3399 forms colonies of cream tint with an even edge and smooth surface. Round or oval-shaped cells (2,-4.5)×(3.5-7.5) μm. Vegetative reproduction occurs by pullulation. Ascospores are globe- or fairly egg-shaped, smooth, 1-4 (more often 3-4) in ascus. Ferments sugars, does not assimilate nitrates. Can develop in substrates with a high content of sugars (up to 80%). Forms a lot of organic acids. In liquid media, it can form both sludge and films.

*Gluconoacetobacter hansenii* strain G-001 represents rods in pairs and chains. On beer, it forms a specific hard leathery film. Does not form endospores. Does not have a brown pigment. Gram-negative. Metabolism—of respiratory type; terminal acceptor—oxygen. Strict aerobe. Optimal conditions for growth: temperature—30° C., pH—5.4-6.3. Produces cellulose. Does not grow at medium with ethanol as a single source. Oxidation of ethanol to acetic acid at neutral and acid medium. Acetic and lactic acid to $CO_2$ and $H_2O$.

The present invention is illustrated by the following examples, which are provided for justification only and are not intended to be limiting the scope of the invention in any way.

EXAMPLES

Example 1

Method for Making a Fermented Base

Maltose concentrates, including kvass wort concentrate, barley-malt extract, high-maltose syrup or brewing syrup, are used as a carbohydrate-containing substrate. Fermentation is performed in four stages. At the first stage a blend from the maltose concentrate is fermented with the use of any bakery yeast or *Zygosaccharomyces bisporus*. At this stage various refeeding supplementations for yeast are added. Initial density of the nutritional medium at the first stage at a level of about 10-15% is reached by diluting a concentrate with treated water. The added amount of yeast and temperature regimes are maintained in accordance with recommendations of manufacturers of feedings and yeast (in particular, ERBSLOEH Geisenheim AG, Germany, manufacturer of feedings "Vitamon A", "Vitamon Kombi", "Vitamon Ultra", and Morgan Thorpe, Belgium, manufacturer of feeding for yeast "Aktivbriu"). Preferably, a culture fluid of *Zygosaccharomyces bisporus* is added in amount of 5.0-10.0% of fermented blend volume. The duration of the first stage of fermentation is 24-48 hours. At the second stage, the second portion of the maltose concentrate in a calculated amount is added into the blend to achieve initial density. At this point the different feedings for yeast and a new batch of fresh yeast cultures are added into the blend. The duration of the second stage is 48 hours. Yeast are precipitated with the use of specific drugs and cooling. The fermented blend is decanted. At the third stage a calculated amount of maltose concentrate added into the blend to achieve a density of 17.0% and culture fluid Gluconabacter hansenii G-001 in amount of 10.0% of fermented blend volume is added into the blend. The fermentation is carried out at a temperature of 35-38° C. The duration of the third stage is 24 hours. At the fourth stage in the blending make maltose concentrate and sugar to achieve the complete formulation values.

Fermentation is carried out up to acidity value of 25 AD. After separation the fermented base is pasteurized by heating up to 80-85° C. for 10 minutes. At the same time volatile substances are distilled out and then returned into a finished concentrate.

Example of Calculation for the Following Formulation of Fermented Base:
beer wort concentrate: 330 kg;
sugar: 10 kg;
water: to 1000 l.
The Source Data of the Technological Process:
Dry matter content in beer wort concentrate: 80.0%;
Density of beer wort concentrate: 1.36.
Initial Density of the Nutritional Medium (Dry Matter Content Before Fermentation):
10.0% (i.e. 1000 liters of the blend must contain 100 kg DM).

Calculation of the Amount of Concentrate to Achieve Initial Density of 10.0% of DM Content at the First Phase, for the Blending Volume of 1000 Liters:

At the first stage 50 kg of sugar, corresponding to 49.9 kg DM, are added into the blend.
The remaining 50.1% DM are added along with the beer wort concentrate.
50.1 kg DM are contained in 62.5 (50:0.8) kg of the concentrate.
To achieve a density of 10.0% DM water is added to 62.5 kg of the beer wort concentrate and 50 kg of sugar; the blend volume is made up to 1000 liters with water.

Calculation of the Amount of Concentrate to Achieve 10.0% of DM Content at the Second Stage:
At the second stage the blend volume is increased to 5000 liters.
To achieve 10.0% of DM content 5000 liters of blend should contain 500 kg DM.
At the completion of the first stage of fermentation, the density is lowered to 8.0%, i.e. 1000 liters of blend contains 80 kg DM.
420 (500-80) kg DM should be added into the blend. 49.9 kg DM are added with 50 kg of sugar.
370.1 kg DM are added with the beer wort concentrate.

370.1 kg DM are contained in 462.6 (370.1:0.80) kg of the beer wort concentrate.

I.e., at the second stage, 50 kg of sugar and 462.6 kg of the beer wort concentrate are added into the blend, and the blend volume is made up to 5000 liters with water.

Calculation of the Amount of Concentrate to Achieve 17.0% of DM Content at the Third Stage:

At the third stage the blend volume is increased to 8000 liters.

To achieve a density of 17.0% of DM content 8000 liters of blend should contain 1360 kg DM.

At the completion of the second stage of fermentation, the density is lowered to 7.0%, i.e. 5000 liters of blend contains 350 kg DM.

1010 (1360-350) kg DM should be added into the blend.

1010 kg DM are contained in 1262.5 (1010:0.8) kg of the beer wort concentrate.

At the third stage, 1262.5 kg of the concentrate is added into the blend, and the blend volume is made up to 8000 liters with water.

Calculation of the Amount of Concentrate at the Fourth Stage:

$62.5_{KT}$ of the concentrate at the first stage, 462.6 kg of the concentrate at the second stage and 1262.5 kg at the third stage have been added into the blend. At the fourth stage, 1512.4 (3300-62.5-462.6-1262.5) kg of the beer wort is added into the blend until the full prescription rules and the blend volume is made up to 10 000 liters with water.

Example 2

Method of Producing Fermented Kvass

Fermented kvass is produced on filling lines for soft drinks at plants lacking own fermentation lines from the fermented base by filling a bottle with a portion of a blend syrup from the fermented base with sugar and other formulation constituents in accordance with a specific formula of kvass followed by diluting it with cold water saturated with carbon dioxide or by mixing water and blend syrup in machines of type <<Postmiks>> and other systems with saturation followed by saturating the blend with carbon dioxide and bottle filling.

Example of one of the formulations of kvass:
Fermented kvass base: 100 l;
sugar: 60 kg;
carbon dioxide;
water: up to 1000 l Example 3

Method of Preparing Alcohol-Free Kvass

Maltose concentrates, including kvass wort concentrate, barley-malt extract, high-maltose syrup, brewing syrup, as well as syrups based on fruits, berries and vegetables, are used as a carbon-containing raw material. Fermentation is performed in four stages. Initial density of the nutritional medium at the first stage at a level ranged from 10% to 15% is reached by diluting a concentrates or syrups with treated water. The duration of the first stage of fermentation with the use of culture fluid *Dekkera anomala* D-001 is 24-48 hours at a temperature of 30-32° C. Culture fluid *Dekkera anomala* D-001 in amount of 10.0-20.0% of fermented blend volume is added into the blend. At the second stage, a portion of the maltose concentrate in a calculated amount is added into the base to achieve the original density. The duration of the second stage is 24-48 hours at a temperature of 30-32° C. At the third stage, to achieve the original density a calculated amount of the concentrate and culture fluid of Gluconabacter hansenii G-001 in amount of about 10.0% of fermented blend volume are added into the base. The fermentation is carried out at a temperature of 32-38° C. The duration of the third stage is 24-48 hours. At the fourth stage a maltose concentrate is added into the blend until the full formulation. The fermentation is carried out at a temperature of 36-38° C. to achieve an alcohol content not exceeding 0.2% and acidity not less 25 AD. After separation, the finished base is pasteurized by heating up to 90-95° C. during 10 minutes. At the same time volatile substances are distilled out. A calculation of maltose concentrate amount is performed as indicated in Example 1, depending on the kvass formulation.

In particular, a non-alcoholic kvass composition was as follows (kvass formulation):

Composition 1 (Low calorie kvass): Water, barley-malt extract, green tea, sourdough, sweetener.

Composition 2 (Mead, non-alcoholic): Water, high-maltose syrup, honey, sugar, sourdough.

Composition 3 (Diabetic kvass): Water, oat-malt extract, green tea, sourdough, stevioside.

Composition 4 (Sbiten, non-alcoholic): Water, honey, sugar, apple juice concentrate, kvass wort concentrate, sourdough, green tea, cumin, cloves, coriander, extracts of sage, mint and thyme.

A variant of the Soft Sbiten kvass formulation includes:
Honey: 50 kg;
Kvass wort concentrate: 30 kg;
Apple juice concentrate: 10 kg;
Starter culture (sourdough) Kombucha on green tea with sugar: 100 l;
Cumin: 0.150 kg;
Cloves: 0.150 kg;
Coriander: 0.150 kg;
Sage extract: 0.015 kg;
Mint extract: 0.015 kg;
Thyme extract: 0.015 kg Example 4

Method for Making Tea Fungus Culture Fluid

To obtain tea fungus culture fluid a culture from the consortium Fungi Tea Sa-14, *Medusomyces gisevii* alfa Sa-10 or *Medusomyces gisevii* SA-12 is used.

Variant 1. A nutritional medium of malt extract containing 5.0-10.0% reducing sugars is pre-fermented in closed tanks with the use of *Zygosaccharomyces bisporus* under optimal for this culture temperatures (32-36° C.); the culture of *Zygosaccharomyces bisporus* is added in amount from 5.0% to 10.0% of the nutritional medium volume. The alcohol formed from the pre-fermentation serves as a source of food and speeds up the work of tea fungus culture. After manifestation of visible signs of fermentation, the consortium culture of Fungi Tea Sa-14, *Medusomyces gisevii* alfa Sa-10 or *Medusomyces gisevii* SA-12 in amount from 10% to 15% of the nutritional medium volume is added into the nutritional medium; when DM content lowering stops the fermentation process is considered to be finished. Under these conditions, tea fungus culture fluid with concentration of living cells at least 30 million/cm$^3$ after resuspension of sediment is obtained.

Variant 2: After manifestation of visible signs of fermentation, the consortium culture a Fungi Tea Sa-14, *Medusomyces gisevii* alfa Sa-10 or *Medusomyces gisevii* SA-12 in amount from 1% to 5% of the nutritional medium volume is added into the nutritional medium; the obtained blend is saturated with filter-sterilized air, over-pressurized and excess pressure and heated to the optimal temperature for that culture (32-36° C.). The saturation of the nutritional medium with air under excess pressure of at least 0.4-0.7 atmosphere at optimum temperatures and in the presence of alcohol accelerates Kombucha by 15-20 times. To prevent the growth of zooglea the growth medium is additionally mixed with the use of circulation 4-6 times per day for 1-2 minutes. When DM content lowering stops the fermentation process is considered to be finished. Under these conditions, tea fungus culture fluid with concentration of living cells at least 30 million/cm$^3$ after resuspension of sediment is obtained.

Example 5

Method for Making Kombucha Concentrates

Tea fungus culture fluid obtained as described in Example 4, is used to produce kombucha concentrates as a starter culture for a concentrated growth medium consisting of fermentable carbohydrates and plant raw materials, included into a specific formulation of the concentrate. To obtain tea concentrates fermented by tea fungus, tea raw materials are placed in special bags, brewed with boiling water with mash ratio 1:10. After cooling to 32° C. tea fungus culture fluid in amount of 10.0% of the volume of fermentable raw materials is added. The process is performed in closed tanks by a zooglea-free way under optimal for this culture temperatures (32-36° C.) until DM content lowering stops. After that the acidity of the nutritional medium is reduced and stabilized using *Gluconoacetobacter hansenii* G-001 or lactic acid bacteria in amount at least 1.0% of the volume of fermentable raw materials. The process is performed until the acidity reaches to a steady state. Tea concentrates fermented by tea fungus are separated, filter-sterilized and packed into clean containers.

When using raw grains as a nutritional medium the raw grain extracts preliminary hydrolyzed with the use of malts and comprising from 13% to 19% DM are pre-fermented with the use of *Zygosaccharomyces bisporus*. After decrease of DM by 5.0-6.0% tea fungus culture fluid in amount of 5.0-10.0% of the volume is added into the nutritional medium. The process is performed in closed tanks by a zooglea-free way until DM content lowering stops.
After reducing and stabilizing the acidity with the use of *Gluconoacetobacter hansenii* G-001 or lactic acid bacteria a calculated amount of the maltose concentrate is added to reach the original density and the blend is ripened at optimal temperatures until stopping the decrease of DM content. The concentrate are separated, filtered and sterilized by boiling or autoclaving. The DM balance is calculated as indicated above in Example 1.

Example 6

Method for Making Kombucha Beverages

To obtain a living Kombucha drink the blend is prepared according to the following scheme: tea fungus culture fluid in a calculated amount (at least 1%) is added into a carbohydrate-containing syrup based on components according to the beverage formula until its acidity and DM content reach formulation values for a freshly prepared beverage. To stabilize the acidity the starter culture from *Gluconoacetobacter hansenii* G-001 in amount about 1.0% of the blend volume is added into the blend. The beverage is ready from the first day of bottling. The maturation of beverage goes on in bottles during the whole shelf life. The beverage will not spoil with keeping during three and more years.

Beverages of different compositions and tastes are obtained depending on used formulation constituents. Diabetic kombucha beverages according to the present invention comprise residual carbohydrates in amounts not exceeding 0.2% if the formulation includes stevia or steviosides. To produce unfiltered and unpasteurized kombucha beverages, in particular, extracts of cereals (oat, buckwheat) or tea (green or black tea), vegetable juices, with spices and salt, are used as a raw material after hydrolysis in the presence of malt enzymes. The use of juices of sauerkraut, cucumbers, apples, watermelon makes the drinks a taste of pickled cabbage, gherkin pickle, pickled apple and pickled watermelon, respectively.

Addition of coffee or chicory to an oatmeal-malt extract gives the drink the original aftertaste.

A milk beverage is obtained with the use of pasteurized skimmed milk as a nutritional medium. A tea fungus culture fluid is added into pasteurized skimmed milk in the ratio 3:1. The obtained blend is ripened at a temperature 20-25° C. during 8-12 hours, cooled to +4° C. and is bottled in consumer packages. Cold shelf storage: not more than 7 days. To produce dairy beverages, in particular, green tea, with stevia or without it, is optionally added into skim milk.

To produce pasteurized kombucha beverages the blend is prepared according to the following scheme: tea fungus culture fluid in amount about 10.0% of the blend volume is added into a carbohydrate-containing syrup based on components according to the beverage formula with sugar content from 5.0 to 10.0%. After glass bottle filling beverage is ripened in camera at a temperature from +30.0 to +35° C. until its acidity reaches formulation values for a freshly prepared beverage. Afterwards it is subjected to tunnel pasteurization or autoclaving. The beverage will not spoil with keeping during 180 days at a temperature from +2 to +25° C. Pasteurized beverages are obtained based on tea and maltose concentrates, honey, skimmed milk, glucose and glucose-fructose syrups, fruits, berries and vegetables.

Dough of rolled oats or oat flour is used as a nutritional medium to produce oat jelly beverages. These beverages can be produced with stevia or without it, with the addition of the choice of berries, in particular, red bilberries, blackberries. The dough of rolled oats or oat flour is fermented using *Zygosaccharomyces bisporus*. To achieve the acidity of formulation the dough is washed through a sieve, large particles remaining on the sieve, and liquid fraction is blended with other constituents according to the formula, brought until boiling on stirring and poured into cans or bottles.

The invention claimed is:
1. A method of culturing a tea fungus for producing a tea fungus culture broth comprising:
the fermentation of a broth containing carbohydrate-containing raw materials by placing a tea fungus culture into said broth for fermentation wherein said broth is treated by aeration under excess pressure and circulated by a circulation pump during a fermentation preventing thereby zooglea formation, and
the tea fungus culture is *Medusomyces gisevii* VKPM SA-12.
2. The method of culturing a tea fungus for producing a tea fungus culture broth according to claim 1, wherein preliminary fermentation is carried out using *Zygosaccha-*

*romyces bisporus* followed by end fermentation using the *Medusomyces gisevii* VKPM SA-12.

3. A method for making kombucha beverages from vegetable juices or vegetables comprising a fermentation of a nutrition media containing vegetable juices or deviled vegetables mixed with salt and spices wherein a fermentation is performed by a tea fungus culture broth of *Medusomyces gisevii* VKPM SA-12 obtained by the method of claim 1.

4. A product obtained by the method of claim 1.

5. The method of culturing a tea fungus for producing a tea fungus culture broth according to claim 1 wherein the pressure is at least 0.4 to 0.7 atmosphere, and the circulation is performed 4 to 6 times per day for 1 to 2 minutes.

* * * * *